United States Patent [19]

Masuzawa et al.

[11] Patent Number: 5,043,450
[45] Date of Patent: Aug. 27, 1991

[54] 8-ALKOXYQUINOLONECARBOXYLIC ACID AND SALTS THEREOF

[75] Inventors: Kuniyoshi Masuzawa, Koga; Seigo Suzue; Keiji Hirai, both of Kuki; Takayoshi Ishizaki, Washimiya, all of Japan

[73] Assignee: Kyorin Pharmaceutical Co., Ltd., Tokyo, Japan

[21] Appl. No.: 600,828

[22] Filed: Oct. 22, 1990

Related U.S. Application Data

[62] Division of Ser. No. 3,822, Jan. 16, 1987, Pat. No. 4,980,470.

[30] Foreign Application Priority Data

Jan. 21, 1986 [JP] Japan .................. 61-10880
Sep. 18, 1986 [JP] Japan .................. 61-220149

[51] Int. Cl.$^5$ .................. C07D 403/04
[52] U.S. Cl. .................. 546/156; 544/225; 544/226; 544/363; 546/8; 556/423; 560/53; 562/840; 562/473; 564/176; 558/423
[58] Field of Search .................. 546/156

[56] References Cited

U.S. PATENT DOCUMENTS

| | | | |
|---|---|---|---|
| 4,665,079 | 5/1987 | Culbertson et al. | 546/156 |
| 4,777,175 | 10/1988 | Culbertson et al. | 546/156 |
| 4,822,801 | 4/1989 | Domagala et al. | 546/156 |
| 4,851,418 | 7/1989 | Sanchez | 546/156 |
| 4,997,943 | 3/1981 | Iwata et al. | 546/156 |

FOREIGN PATENT DOCUMENTS

| | | |
|---|---|---|
| 0106489 | 4/1984 | European Pat. Off. |
| 0126355 | 11/1984 | European Pat. Off. |
| 0132845 | 2/1985 | European Pat. Off. |
| 0153163 | 8/1985 | European Pat. Off. |
| 0153828 | 9/1985 | European Pat. Off. |
| 0342675 | 11/1989 | European Pat. Off. |

Primary Examiner—C. Warren Ivy
Assistant Examiner—James H. Turnipseed
Attorney, Agent, or Firm—Oblon, Spivak, McClelland, Maier & Neustadt

[57] ABSTRACT

Quinolonecarboxylic acid derivatives of the following formula,

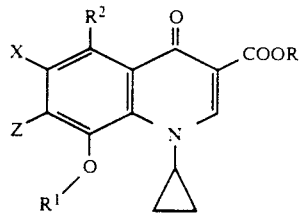

wherein R indicates a hydrogen atom or lower alkyl group, $R^1$ indicates a lower alkyl group, $R^2$ indicates a hydrogen atom, amino group or nitro group, X indicates a halogen atom, and Z indicates a halogen atom, piperazino group, N-methylpiperazino group, 3-methylpiperazino group, 3-hydroxypyrrolidino group, or pyrrolidino group of the following formula,

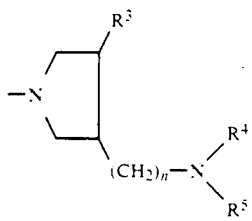

(here, n is 0 or 1, $R^3$ indicates a hydrogen atom or lower alkyl group, $R^4$ indicates a hydrogen atom, lower alkyl group or substituted lower alkyl group and $R^5$ indicates a hydrogen atom, lower alkyl group, acyl group or alkoxycarbonyl group), the hydrates and pharmaceutically acceptable salts thereof are useful as antibacterial agents.

5 Claims, No Drawings

8-ALKOXYQUINOLONECARBOXYLIC ACID AND SALTS THEREOF

This is a division of application Ser. No. 003,822, filed on Jan. 16,1987, now U.S. Pat. No. 4,980,470.

DETAILED DESCRIPTION OF THE INVENTION

The present invention relates to novel quinolonecarboxylic acid derivatives having excellent properties as antibacterial agent, process for their preparation, and antibacterial agents containing these novel compounds.

Compounds of this invention are characterized in having a cyclopropyl group on 1-position and an alkoxy group on 8-position of the quinolonecarboxylic acid.

With respect to the 8-alkoxyquinolonecarboxylic acid derivatives, following 8-methoxy derivatives were described previously in Japanese Unexamined Patent Publication No. Sho 60-214773.

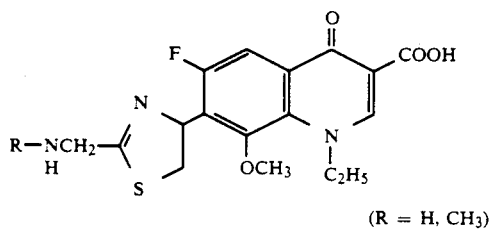

(R = H, CH₃)

However, the antibacterial activity of those compounds is weak and their other favorable properties for antibacterial agents have not been described.

Recently, norfloxacin, which has been developed by us, shows high antibacterial activity against gram-negative bacteria including *Pseudomonas aeruginosa* and gram-positive bacteria. This compound is widely used clinically as new quinolonecarboxylic acid-antibacterial agent having a broad antibacterial spectrum. Afterwards, efforts are focusing on improvement of bioavailability of norfloxacin or strengthing its antibacterial activity.

Consequently, quinolonecarboxylic acid derivatives, having similar substituents, such as ofloxacin and ciprofloxacin have been developed. These new quinolonecarboxylic acid derivatives show more excellent antibacterial activity against gram-negative bacteria than other antibacterial agents such as β-lactam and aminoglycoside antibiotics. Moreover, the development and spread of resistance to new quinolonecarboxylic acids is not easy as compared with that of other antibacterial agents. However, their activity against gram-positive bacteria are weak compared with those against gram-negative bacteria. Therefore, these quinolonecarboxylic acids have unfortunately solved the clinical problem of increase in the isolation frequency of gram-positive bacteria from clinical materials. From the results of various studies, the inventors found that some of the quinolonecarboxylic acid derivatives having excellent antibacterial activity can not use as medicinal drug because of their toxicity, and that excellent selective toxicity is important factor as well as antibacterial activity.

As the results of diligent studies focusing on the dissolution these problem and on the development of useful new medicinal drugs, the inventors have found novel compounds of this invention exhibit extremely high activity against aerobic gram-negative and -positive bacteria, and besides anaerobic bacteria and Mycoplasma that show less susceptibility to conventional quinolonecarboxylic acids. Furthermore, these compounds show not only high selective toxicity between prokaryotic cells and eukaryotic cells, but also the excellent absorption when administered to animals orally. The compounds of this invention do not exhibit any toxicological effects after oral or parenteral administration.

These indicates that the compounds of this invention are very useful as the medicinal drugs for human being and domestic animals, and further as antibacterial agents for fish and shellfish, and plants.

The invention provides 8-alkoxyquinolonecarboxylic acid derivatives represented by a general formula (I),

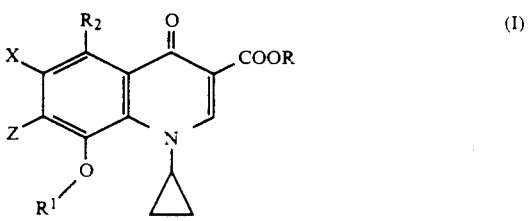

wherein R indicates a hydrogen atom or lower alkyl group, $R^1$ indicates a lower alkyl group, $R^2$ indicates a hydrogen atom, amino group or nitro group, X indicates a halogen atom, and Z indicates a halogen atom, piperazino group, N-methylpiperazino group, 3-methylpiperazino group, 3-hydroxypyrrolidino group, or pyrrolidino group of the following formula,

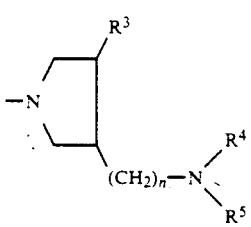

(here, n is 0 or 1, $R^3$ indicates a hydrogen atom or lower alkyl group, $R^4$ indicates a hydrogen atom, lower alkyl group or substituted lower alkyl group and $R^5$ indicates a hydrogen atom, lower alkyl group, acyl group or alkoxycarbonyl group), the hydrates or the pharmaceutically acceptable acid addition or alkali salts thereof.

Here, the lower alkyl group means a straight or branched alkyl group having carbon atom of 1 to 5, for example, methyl group, ethyl group, isopropyl group, n-butyl group, t-butyl group, amyl group, isoamyl group or the like.

Moreover, the halogen atom means a fluorine atom, chlorine atom, bromine atom or iodine atom, preferably fluorine atom, chlorine atom or bromine atom.

The acyl group means an aliphatic or aromatic acyl group having carbon atoms of 1 to 10, for example, formyl group, acetyl group, benzoyl group or the like.

The alkoxycarbonyl group means an aliphatic or aromatic alkoxycarbonyl group having carbon atoms of 1 to 10, for example, ethoxycarbonyl group, t-butoxycarbonyl group, benzyloxycarbonyl group or the like.

The substituted lower alkyl group means a previously defined alkyl group being substituted with hydroxy group or halogen atom, for example, hydroxyethyl group, fluoroethyl group or the like.

In following, the processes of preparing the compounds of the invention will be explained.

Compounds represented by a general formula (IV);

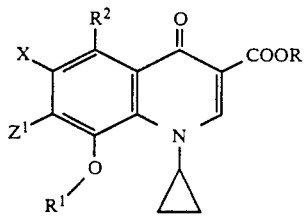
(IV)

wherein R, $R^1$, $R^2$ and X are same as above, and $Z^1$ indicates a piperazino group, N-methylpiperazino group, 3-methylpiperazino group, 3-hydroxypyrrolidino group, or pyrrolidino group of the following formula,

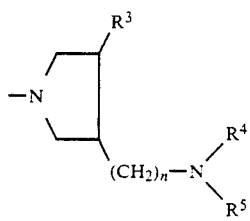

(here, n, $R^3$, $R^4$ and $R^5$ are same as above.) are prepared by allowing compounds represented by a general formula (II);

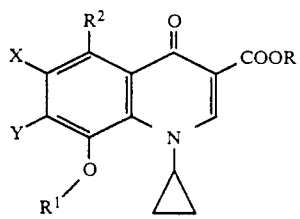
(II)

wherein Y indicates a halogen atom, and R, $R^1$, $R^2$ and X are same as above, to condense with cyclic amines represented by a general formula (III);

$Z^1$—H  (III)

wherein $Z^1$ is same as above.

The reaction between the compounds represented by the formula (II) and the compounds represented by the formula (III) can be conducted in the absence of solvent or in the presence of polar solvents such as water, alcohols, acetonitrile, dimethylformamide (DMF), dimethyl sulfoxide (DMSO), hexamethylphosphoric amide (HMPA , pyridine, picoline, etc. The reaction temperature is selected appropriately within a range of room temperature to 200° C., preferably room temperature to 160° C. In more detail, it is suitable to allow the compounds represented by the formula (II) to react with 1 to 5 times mole of the compounds represented by the formula (III) for 1 to 50 hours at room temperature to 120° C. in 2 to 10 times volume of the solvents aforementioned per volume of the compound (II).

At this time, the use of deacidifying agents such as triethylamine, diazabicyclo bases and potassium carbonate is also preferable.

Moreover, in the case of compounds in which R is a lower alkyl group, that is, compounds represented by a general formula (V);

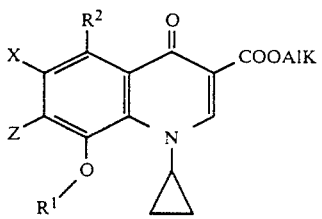
(V)

wherein Alk indicates a lower alkyl group, and $R^1$, $R^2$, X and Z are same as above, among the compounds represented by the general formula (I), they are converted to quinolonecarboxylic acid derivatives represented by a general formula (VI);

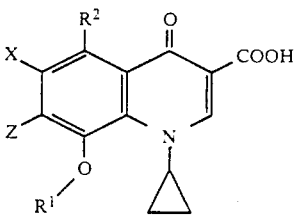
(VI)

wherein $R^1$, $R^2$, X and Z are same as above, by hydrolyzing according to usual method.

Such hydrolysis can be carried out easily at room temperature to boiling point of solvent in water, alcohols or mixed solutions thereof using alkalies such as sodium hydroxide and potassium hydroxide or acids such as hydrochloric acid and sulfuric acid.

Next, among the compounds represented by the general formula (I), compounds represented by a general formula (VII);

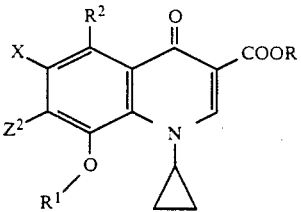
(VII)

wherein $Z^2$ indicates pyrrolidino group of the following formula,

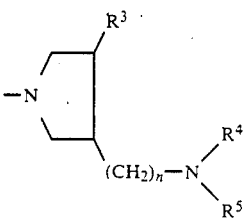

(here, $R^6$ indicates an acyl group or alkoxycarbonyl group, and n, $R^3$ and $R^4$ are same as above), and R, $R^1$, $R^2$ and X are same as above, can be converted to compounds represented by a general formula (VIII);

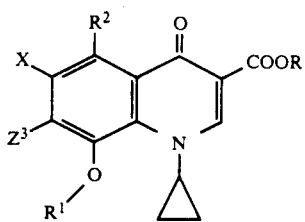
(VIII)

wherein $Z^3$ indicates pyrrolidino group of the following formula,

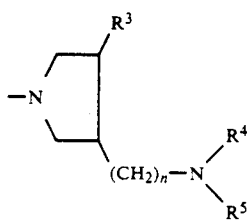

(here, $R^3$ and $R^4$ are same as above.), and R, $R^1$, $R^2$ and X are same as above, by submitting to deacylation.

Such reaction can be carried out easily by the methods well known usually such as hydrolysis with acid or alkali catalyst, catalytic reduction, etc.

The synthetic intermediates represented by the general formula (II) for the preparation of the compounds of the invention are also novel compounds and can be prepared through, for example, following route.

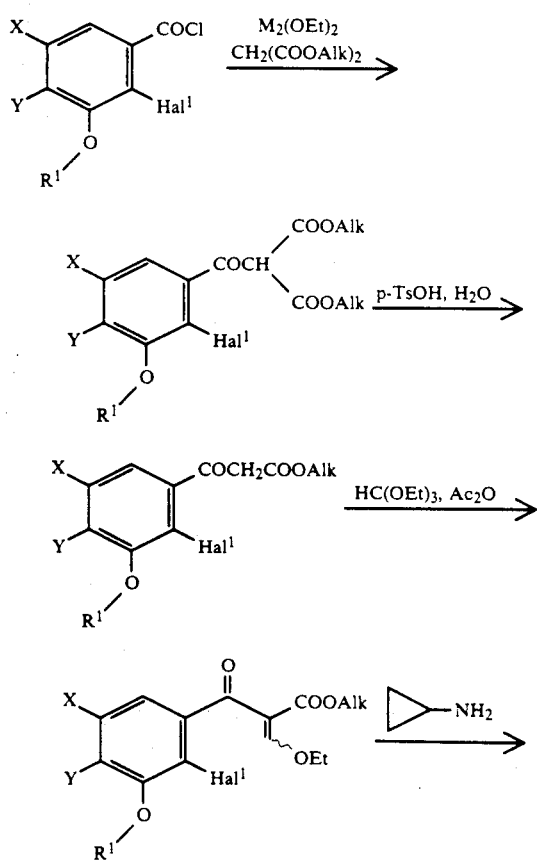

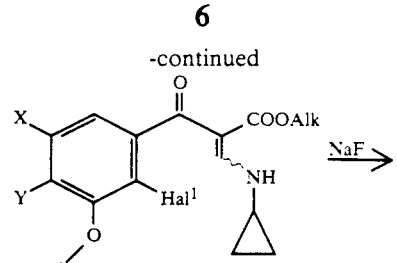

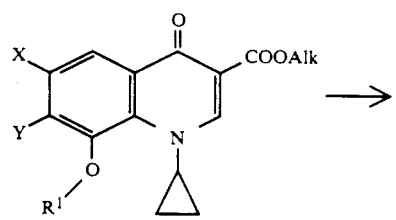

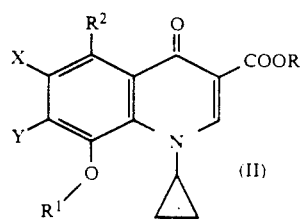
(II)

(wherein $Hal^1$ indicates a halogen atom, and Alk, R, $R^1$, $R^2$, X and Y are same as above.)

The compounds of the invention represented by the general formula (I) can also be prepared by allowing compounds represented by a general formula (IX) to act with alcohols represented by a general formula (X) as follows:

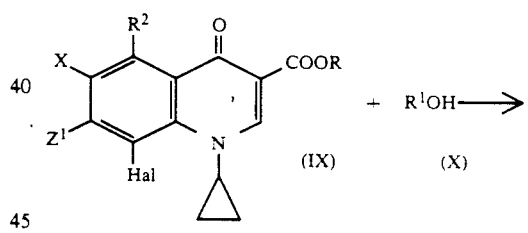

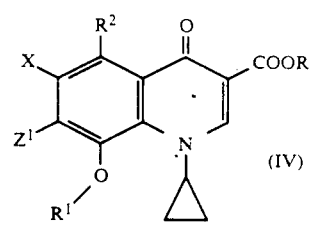
(IV)

wherein Hal indicates a halogen atom, and R, $R^1$, $R^2$, X and $Z^1$ are same as above.

Such reaction is carried out without solvent or in the solvents such as alcohols, acetonitrile, DMSO, DMF, HMPA, dioxane, benzene, etc. in the presence of deacidifying agent, and it is desired to be carried out under anhydrous condition in order to suppress the side reactions. As the deacidifying agents, alkali fluoride, alkali metal alcoholate, alkali hydride, etc. can be used, but it is suitable to use alcohols represented by a general formula $R^1OH$ as solvents, to allow these to act with alkali metals such as sodium, potassium, lithium, etc., and to submit to the reaction as they are.

In more detail, it is suitable to allow the compounds represented by the formula (IX) to react with at least not less than equivalent moles of foregoing deacidifying agent and alcohols represented by the general formula $R^1OH$ for 1 to 200 hours at room temperature to 200° C. in 1 to 50 times volume of foregoing solvents per volume of the compound (IX), and, when using low boiling point solvents, it is more advantageous to allow to react at high temperature in a sealed tube.

Next, the compounds represented by the formula (I) can be converted to the salts thereof according to usual method, if necessary. As the salts, for example, those with inorganic acids such as hydrochloric acid, sulfuric acid, phosphoric acid, etc., those with organic acids such as methanesulfonic acid, lactic acid, oxalic acid, acetic acid, etc., or salts of sodium, potassium, magnesium, calcium, aluminum, cerium, chromium, cobalt, copper, iron, zinc, platinum, silver, etc. can be mentioned.

Furthermore, when the compounds of the invention are administered to human being or animals and plants, the shapes and the routes well known pharmaceutically up to this time are applied. They are used orally or parenterally through, for example, powders, tablets, capsules, ointments, injections, syrups. liquids, eye drops, suppositories, etc.

The following examples will further illustrate the invention without, however, limiting it thereto.

EXAMPLE 1

Synthesis of 1-cyclopropyl-6-fluoro-1,4-dihydro-8-methoxy-4-oxo-7-(1-piperazinyl -3-quinolinecarboxylic acid A mixture of 1-cyclopropyl-6,7-difluoro-1,4-dihydro-8-methoxy-4-oxo-3-quinolinecarboxylic acid (200 mg), anhydrous piperazine (180 mg) and anhydrous dimethyl sulfoxide (DMSO; 3 ml) was stirred for 2.5 hours at 70° to 80° C. on an oil bath. The reacting mixture was concentrated under reduced pressure and cold water was added to the residue. The precipitate was collected by filtration and recrystallized from a mixed solution of dichloromethane-methanol (1:1) to give the title compound (40 mg) as pale yellow prisms, mp 187° C. (decompd.).

Analysis (%) for $C_{18}H_{20}FN_3O_4.2\ H_2O$; Calcd. (Found): C, 54.40 (53.96); H, 6.09 (5.99); N, 10.57 (10.34).

EXAMPLE 2

Synthesis of 1-cyclopropyl-6-fluoro-1,4-dihydro-8-methoxy-7-(4-methyl-1-piperazinyl)-4-oxo-3-quinolinecarboxylic acid A mixture of 1-cyclopropyl-6,7-difluoro-1,4-dihydro-8-methoxy-4-oxo-3-quinolinecarboxylic acid (200 mg), N-methylpiperazine (140 mg) and anhydrous DMSO (3 ml) was stirred for 5 hours at 70° to 95° C. on an oil bath. The reacting mixture was concentrated under reduced pressure. The resulting residue was purified by silica gel column chromatography eluting with chloroform-methanol-concentrated aqueous ammonia (20:6:1), the residue was recrystallized from methanol to give the title compound (50 mg) as colorless needles, mp 221°-222° C. (decompd.).

Analysis (%) for $C_{19}H_{22}FN_3O_4$; Calcd. (Found): C. 60.79 (60.82); H, 5.91 (5.90); N, 11.19 (11.24).

EXAMPLE 3

Synthesis of 1-cyclopropyl-6-fluoro-1,4-dihydro-8-methoxy-7-(3-methyl-1-piperazinyl)-4-oxo-3-quinolinecarboxylic acid A mixture of 1-cyclopropyl-6,7-difluoro-1,4-dihydro-8-methoxy-4-oxo-3-quinolinecarboxylic acid (200 mg), 2-methylpiperazine (140 mg) and anhydrous DMSO (3 ml) was stirred for 2 hours at 70° to 95° C. on an oil bath. The reaction mixture was concentrated under reduced pressure. The resulting residue was purified by silica gel column chromatography eluting with chloroform-methanol-concentrated aqueous ammonia (20:6:1), the residue was recrystallized from methanol to give the title compound (50 mg as white powdery crystals, mp 162°- C.

Analysis (%) for $C_{19}H_{22}FN_3O_4.\frac{1}{2}\ H_2O$; Calcd. (Found): C, 59.37 (59.95); H, 6.03 (6.01); N, 10.93 (10.81).

EXAMPLE 4

Synthesis of 7-(3-amino-1-pyrrolidinyl)-1-cyclopropyl-6-fluoro-1,4-dihydro-8-methoxy-4-oxo-3-quinolinecarboxylic acid To a suspension of 1-cyclopropyl-6,7-difluoro-1,4-dihydro-8-methoxy-4-oxo-3-quinolinecarboxylic acid (2 g) in anhydrous acetonitrile were added 3-t-butoxycarbonylaminopyrrolidine (1.86 g) and 1,8-diazabicyclo[5,4,0]undec-7-en (DBU, 1.02 g) and then the mixture was refluxed for 3 hours. The reaction mixture was concentrated under reduced pressure and the residue was dissolved in chloroform (50 ml). The resulting solution was washed with 10% aqueous citric acid solution (20 ml), and with saturated saline solution successively. The organic layer was dried over anhydrous sodium sulfate and then concentrated. The residue was dissolved in hot methanol (20 ml) and then cooled. The resulting crystals were collected by filtration to give 7-(3-t-butoxycarbonylamino-1-pyrrolidinyl)-1-cyclopropyl-1,4-dihydro-6-fluoro-8-methoxy-4-oxo-3-quinolinecarboxylic acid (2.25 g) as yellowish white prisms, mp 224°-226° C. (decompd.).

Analysis (%) for $C_{23}H_{28}FN_3O_6.\frac{1}{4}\ H_2O$; Calcd. (Found): C. 59.28 (59.18); H, 6.22 (6.08); N, 9.02 (8.82).

To a suspension of these crystals (2.23 g) in methanol (16 ml) was added concentrated hydrochloric acid (16 ml) dropwise. After stirring for 3 hours at room temperature, the reaction mixture was cooled and neutralized with concentrated aqueous ammonia. The resulting precipitate was collected by filtration and washed with methanol and ether successively to give the title compound (1.52 g) as white powder, mp 217°-218° C.

Analysis (%) for $C_{18}H_{20}FN_3O_4.\frac{1}{2}\ H_2O$; Calcd. (Found): C. 58.37 (58.68); H, 5.71 (6.10); N, 11.35 (11.14).

EXAMPLE 5

Synthesis of 7-(cis-3-amino-4-methyl-1-pyrrolidinyl)-1-cyclopropyl-6-fluoro-1,4-dihydro-8-methoxy-4-oxo-3-quinolinecarboxylic acid A mixture of 1-cyclopropyl-6,7-difluoro-1,4-dihydro-8-methoxy-4-oxo-3-quinolinecarboxylic acid (200 mg), cis-3-t-butoxycarbonylamino-4-methylpyrrolidine (150 mg), DBU (110 mg) and anhydrous acetonitrile (3 ml) was refluxed for 5 hours. After cooling, the resulting precipitate was collected by filtration. This precipitate was added to the mixture of concentrated hydrochloric acid-methanol (1:1, 6 ml) and stirred for 1.5 hours at room temperature. The reaction mixture was neutralized by concentrated aqueous ammonia and allowed to stand in the refrigerator. The resulting crystals were collected by filtration and washed with cold water to give the title compound (90 mg) as colorless prisms, mp 185°–188° C. (decompd.).

Analysis (%) for $C_{19}H_{22}FN_3O_4 \cdot 3/2\ H_2O$; Calcd. (Found): C, 56.71 (56.53); H, 6.26 (6.17); N, 10.44 (10.37).

EXAMPLE 6

Synthesis of 7-(trans-3-amino-4-methyl-1-pyrrolidinyl)-1-cyclopropyl-6-fluoro-1,4-dihydro-8-methoxy-4-oxo-3-quinolinecarboxylic acid A mixture of 1-cyclopropyl-6,7-difluoro-1,4-dihydro-8-methoxy-4-oxo-3-quinolinecarboxylic acid (0.40 g), trans-3-t-butoxycarbonylamino-4-methylpyrrolidine (0.41 g), DBU (0.21 g) and anhydrous acetonitrile (5 ml) was refluxed for 2.5 hours and then the reaction mixture was concentrated under reduced pressure. The residue was dissolved in chloroform (40 ml) and washed with 10% aqueous citric acid solution (20 ml) and with saturated saline (20 ml) successively. The organic layer was dried over anhydrous sodium sulfate and then concentrated under reduced pressure. The residue was crystallized from ethanol to give 7-(trans-3-t-butoxycarbonylamino-4-methyl-1-pyrrolidinyl)-1-cyclopropyl-6-fluoro-1,4-dihydro-8-methoxy-4-oxo-3-quinolinecarboxylic acid. To a suspension of these crystals in methanol (5 ml) was added concentrated hydrochloric acid (5 ml) dropwise. After stirring for 1.5 hours at room temperature, the reaction mixture was neutralized with concentrated aqueous ammonia, the resulting crystals were collected by filtration and washed with water sufficiently to give the title compound (0.29 g) as colorless powder, mp 214°–215° C.

Analysis (%) for $C_{19}H_{22}FN_3O_4$; Calcd. (Found): C, 60.07 (60.41): H, 5.97 (5.80); N, 11.06 (11.05).

Referential Example 1

Synthesis of 3-methoxy-2,4,5-trifluorobenzoic acid

According to the method by Bardon et al. (Tetrahedron, 22, 2541 (1966)), 1,2,3,4-tetrafluorobenzene (50 g) was brominated and methoxylated to give 1-bromo-3-methoxy-2,4,5-trifluorobenzene (22.2 g) as colorless oil.

A mixture of the oily product (22 g), cuprous cyanide (10 g) and N-methyl-2-pyrrolidone (37 ml) in sealed tube was heated for 4.5 hours at 140° to 150° C. After cooling, a solution of ferric chloride hexahydrate (44 g) and concentrated hydrochloric acid (11 ml) in water (60 ml) was added to the reaction mixture and then stirred at 50° to 60° C. for 20 minutes. The reaction mixture was extracted with ether and the organic layer was washed with dilute aqueous hydrochloric acid, with water and with saturated saline solution successively, and dried over anhydrous sodium sulfate and then concentrated. The residue was purified by distillation under reduced pressure to give 3-methoxy-2,4,5-trifluorobenzonitrile (14.25 g) as colorless oil, bp 94° C./8 mmHg.

To oily product thus obtained (14.2 g) were added concentrated sulfuric acid (8.5 ml) and water (40 ml) and the mixture was stirred for 1 hour at 110° C. After cooling, the reaction mixture was poured into ice water (50 ml) and the resulting precipitate was collected by filtration, washed with water, and recrystallized from a solution of dichloromethane-n-hexane to give 3-methoxy-2,4,5-trifluorobenzamide (11.59 g) as white needle, mp 130°–133° C.

Then, to these crystals were added 18N sulfuric acid (150 ml) and the mixture was heated for 3.5 hours at 100° C. After cooling, water (400 ml) was added to the mixture and the resulting crystals were recrystallized from n-hexane to give the title compound (9.61 g) as colorless needle, mp 98°–101° C.

Analysis (%) for $C_8H_5F_3O_3$; Calcd. (Found): C, 46.62 (46.68); H, 2.45 (2.48).

Referential Example 2

Synthesis of 1-cyclopropyl-6,7-difluoro-1,4-dihydro-8-methoxy-4-oxo-3-quinolinecarboxylic acid To 3-methoxy-2,4,5-trifluorobenzoic acid (9.4 g) was added thionyl chloride (50 ml), the mixture was refluxed for 3 hours and then concentrated. The residue was purified by distillation under reduced pressure to give 3-methoxy-2,4,5-trifluorobenzoyl chloride (8.86 g) as yellow oil, bp 108–112° C./20 mmHg.

To magnesium ethoxide (5.9 g) was added diethyl malonate (7 g) in anhydrous toluene (35 ml) dropwise and the mixture was warmed for 2 hours at 50° to 60° C. and then cooled to −10° C. To the mixture was added a solution of the acid chloride (8.86 g) in anhydrous toluene (10 ml) dropwise over 15 minutes. After stirring for 1 hour at −5° to 0° C., ice water (30 ml) containing concentrated sulfuric acid (8 ml) was added to the mixture and the organic layer was separated. The organic layer was washed with saturated saline solution, dried over anhydrous sodium sulfate and then concentrated to give diethyl 3-methoxy-2,4,5trifluorobenzoylmalonate (13.64 g) as brown oil.

To oily product, the malonate (13.55 g) were added water (20 ml) and p-toluenesulfonic acid (14 mg), and the mixture was refluxed for 9 hours. After cooling, the reaction mixture was extracted with dichloromethane and the organic layer was washed with 7% aqueous sodium bicarbonate solution and with saturated saline solution succesively, dried over anhydrous sodium sulfate and then concentrated to give ethyl 3-methoxy-2,4,5-trifluorobenzoylacetate (10.29 g).

To the benzoyl acetate (9.79 g) were added acetic anhydride (9.6 g) and ethyl orthoformate (8.4 g), and the mixture was refluxed for 3 hours. After supplemented further acetic anhydride (3.2 g) and ethyl orthoformate (8.8 g , the mixture was refluxed for 8 hours, and then concentrated to give ethyl 2-(3-methoxy-2,4,5-trifluorobenzoyl)-3-ethoxyacrylate (9.73 g) as brown oil.

To a solution of the acrylate (9.73 g) in ethanol (20 ml) was added cyclopropylamine (2.0 g) dropwise under cooling. After stirring for 2 hours at room temperature, the reaction mixture was concentrated and the residue was purified by silica gel column chromatography eluting with n-hexane-ethyl acetate (5:1) to give ethyl 2-(3-methoxy-2,4,5-trifluorobenzoyl)-3-cyclopropylaminoacrylate (7.52 g) as yellowish white crystals, mp 56°–58° C.

Analysis (%) for $C_{16}H_{16}F_3NO_4$; Calcd. (Found): C, 55.98 (56.07); H, 4.70 (4.66); N, 4.08 (4.07).

The mixture of the aminoacrylate (6.68 g), sodium fluoride (1.31 g) and anhydrous dimethylformamide (26 ml) was refluxed for 5 hours. After cooling, the reaction mixture was poured into ice water (100 ml) and the resulting precipitate was collected by filtration, washed with water and recrystallized from ethyl acetate to give ethyl 1-cyclopropyl-6,7-difluoro-1,4-dihydro-8-methoxy-4-oxo-3-quinolinecarboxylate (4.53 g) as colorless needle, mp 178°–180° C.

Analysis (%) for $C_{16}H_{15}F_2NO_4$; Calcd. (Found): C, 59.44 (59.34); H, 4.68 (4.59); N, 4.33 (4.33).

To these crystals (4.5 g) was added a mixed solution of acetic acid (30 ml), concentrated sulfuric acid (4 ml) and water (22 ml), and the mixture was refluxed for 1 hour. After cooling, ice water (100 ml) was added and the resulting precipitate was collected by filtration, washed with water and then dried to give title compound (4 g) as colorless powder, mp 185°–186° C.

Analysis (%) for $C_{14}H_{11}F_2NO_4$; Calcd. (Found): C, 56.95 (56.68); H, 3.76 (3.70); N, 4.74 (4.74).

EXAMPLE 7

Synthesis of 7-(3-aminomethyl-1-pyrrolidinyl)-1-cyclopropyl-6-fluoro-1,4-dihydro-8-methoxy-4-oxo-3-quinolinecarboxylic acid A mixture of 1-cyclopropyl-6,7-difluoro-1,4-dihydro-8-methoxy-4-oxo-3-quinolinecarboxylic acid (200 mg), 3-aminomethylpyrrolidine (80 mg), DBU (110 mg) and anhydorous acetonitrile (3 ml) was refluxed for 2.5 hours. After cooling, the resulting precipitate was collected by filtration and recrystallized from a solution of dichloromethane-methanol (1:1) to give the title compound (90 mg) as white powdery crystals, mp 198°–200° C.

Analysis (%) for $C_{19}H_{22}FN_3O_4$; Calcd. (Found): C, 60.79 (60.39); H, 5.91 (5.87); N, 11.19 (11.07).

EXAMPLE 8

Synthesis of 1-cyclopropyl-6-fluoro-1,4-dihydro-8-methoxy-7-(3-methylaminomethyl-1-pyrrolidinyl)-4-oxo-3-quinolinecarboxylic acid A mixture of 1-cyclopropyl-6,7-difluoro-1,4-dihydro-8-methoxy-4-oxo-3-quinolinecarboxylic acid (200 mg), 3-methylaminomethylpyrrolidine (90 mg), DBU (110 mg) and anhydrous acetonitrile (3 ml) was refluxed for 75 minutes. After cooling, the resulting precipitate was collected by filtration and recrystallized from a solution of dichloromethane-methanol (1:1) to give the title compound (130 mg) as white powdery crystals, mp 226.5°–230° C.

Analysis (%) for $C_{20}H_{24}FN_3O_4.\frac{1}{2}$ $H_2O$; Calcd. (Found): C, 60.29 (60.49); H, 6.32 (6.08); N, 10.54 (10.48).

EXAMPLE 9

Synthesis of 1-cyclopropyl-7-(3-ethylaminomethyl-1-pyrrolidinyl)-6-fluoro-1,4-dihydro-8-methoxy-4-oxo-3-quinolinecarboxylic acid A mixture of 1-cyclopropyl-6,7-difluoro-1,4-dihydro-8-methoxy-4-oxo-3-quinolinecarboxylic acid (200 mg), 3-ethylaminomethylpyrrolidine (100 mg), DBU (110 mg) and anhydrous acetonitrile (3 ml) was refluxed for 6 hours. After cooling, the resulting precipitate was collected by filtration and recrystallized from methanol to give the title compound (120 mg) as colorless prisms, mp 217°–219° C.

Analysis (%) for $C_{21}H_{26}FN_3O_4.\frac{2}{3}$ $H_2O$; Calcd. (Found): C, 60.71 (60.59); H, 6.63 (6.43); N, 10.11 (10.03).

Referential Example 3

Synthesis of 1-cyclopropyl-6,7-difluoro-1,4-dihydro-8-methoxy-5-nitro-4-oxo-3-quinolinecarboxylic acid To a solution of 1-cyclopropyl-6,7-difluoro-1,4-dihydro-8-methoxy-4-oxo-3-quinolinecarboxylic acid (490 mg) in concentrated sulfuric acid (5 ml) was added potassium nitrate (235 mg) below 5° C. under stirring portionwise. After stirring for 45 minutes, the reaction mixture was poured into ice water (25 ml) and the resulting precipitate was collected by filtration, washed with cold water sufficiently, recrystallized from a solution of dichloromethane-methanol (1:1) to give the title compound (392 mg) as yellow prisms, mp 215.5°–221° C. (decompd.).

Analysis (%) for $C_{14}H_{10}F_2N_2O_6$; Calcd. (Found): C, 49.42 (49.37); H, 2.96 (2.94); N, 8.23 (8.12).

Referential Example 4

Synthesis of 5-amino-1-cyclopropyl-6,7-difluoro-1,4-dihydro-8-methoxy-4-oxo-3-quinolinecarboxylic acid To a solution of 1-cyclopropyl-6,7-difluoro-1,4-dihydro-8-methoxy-5-nitro-4-oxo-3-quinolinecarboxylic acid (322 mg) in ethanol-DMF (4:1) was added 10% palladium-carbon (25 mg) and the mixture was stirred in hydrogen gas atomosphere for 6 hours at room temperature. The catalyst was filtered off and washed with a solution of chloroform-methanol-concentrated aqueous ammonia (10:10:3) The filtrate and washings were combined and concentrated. The residue was recrystallized from a solution of chloroform-methanol-concentrated aqueous ammonia (20:6:1) to give the title compound (183 mg) as yellow prisms, mp 291°–291.5° C. (decompd.).

Analysis (%) for $C_{14}H_{12}F_2N_2O_4$; Calcd. (Found): C, 54.20 (54.46); H, 3.90 (3.89); N, 9.03 (8.97).

Example 10

Synthesis of 5-amino-1-cyclopropyl-6-fluoro-1,4-dihydro-8-methoxy-4-oxo-7-(1-piperazinyl)-3-quinolinecarboxylic acid A mixture of 5-amino-1-cyclopropyl-6,7-difluoro-1,4-dihydro-8-methoxy-4-oxo-3-quinolinecarboxylic acid (72 mg), anhydrous piperazine (60 mg) and anhydrous DMSO (3 ml) was stirred for 2 hours at 70° to 80° C. and then concentrated under reduced pressure. A solution of the residue into aqueous ethanol acidified with concentrated hydrochloric acid below pH 1. The solution was allowed to stand in a refrigerator. The resulting precipitate was collected by filtration and washed with aqueous ethanol, then with ethanol to give the title compound (33 mg) as yellow flaky crystals, mp 271°–273° C. (decompd.).

Analysis (%) for $C_{18}H_{21}FN_4O_4 \cdot HCl \cdot H_2O$; Calcd. (Found): C, 50.18 (50.28); H, 5.61 (5.48); N, 13.00 (12.97).

EXAMPLE 11

Synthesis of 5-amino-7-(3-amino-1-pyrrolidinyl)-1-cyclopropyl-6-fluoro-1,4-dihydro-8-methoxy-4-oxo-3-quinolinecarboxylic acid A mixture of 5-amino-1-cyclopropyl-6,7-difluoro-1,4-dihydro-8-methoxy-4-oxo-3-quinolinecarboxylic acid (90 mg), 3-t-butoxycarbonylaminopyrrolidine (115 mg), DBU (50 mg) and anhydrous acetonitrile (4 ml) was refluxed for 20 hours. After cooling, the resulting precipitate was collected by filtration and added to concentrated hydrochloric acid-methanol (1:1, 2 ml). The mixture was stirred for 10 minutes at room temperature, then neutralized with concentrated aqueous ammonia, and the precipitate was collected by filtration. A solution of the precipitate in cold water was acidified with concentrated hydrochloric acid below pH 1 and allowed to stand in a refrigerator. The resulting precipitate was collected by filtration and washed with cold diluted aqueous hydrochloric acid to give the title compound (35 mg) as yellow needles, mp 254°–257° C. (decompd.).

Analysis (%) for $C_{18}H_{21}FN_4O_4 \cdot 2\, HCl$; Calcd. (Found): C, 48.12 (48.16); H, 5.16 (5.53); N, 12.47 (12.52).

EXAMPLE 12

Synthesis of 1-cyclopropyl-6-fluoro-1,4-dihydro-8-methoxy-4-oxo-7-(1-piperazinyl)-3-quinolinecarboxylic acid To the solution of sodium methoxide prepared from sodium (0.2 g) and absolute ethanol (9 ml) was added 1-cyclopropyl-6,8-difluoro-1,4-dihydro-4-oxo-7-(1-piperazinyl)-3-quinolinecarboxylic acid (0.5 g) and the mixture in sealed tube was heated for 72.5 hours at 140° to 150° C. After cooling, the reaction mixture was concentrated, water (4 ml) was added to the residue, and the solution was adjusted to pH 7 with acetic acid. The insoluble materials were filtered off and the filtrate was allowed to stand in a refrigerator. The resulting precipitate was collected by filtration and recrystallized from dichloromethane-methanol (2:1; 6 ml) to give the title compound (0.12 g) as colorless prisms, mp 185°–187.5° C. (decompd.).

Analysis (%) for $C_{18}H_{20}FN_3O_4 \cdot \frac{1}{2}\, H_2O$; Calcd. (Found): C, 58.37 (57.98); H, 5.71 (5.52); N, 11.35 (11.28).

EXAMPLE 13

Synthesis of 1-cyclopropyl-6-fluoro-1,4-dihydro-8-methoxy-7-(4-methyl-1-piperazinyl)-4-oxo-3-quinolinecarboxylic acid In a mixture of sodium formate (22 mg), 87% formic acid (0.3 ml) and 37% formalin (25 μl) and 1-cyclopropyl-6-fluoro-1,4-dihydro-8-methoxy-4-oxo-7-(1-piperazinyl)-3-quinolinecarboxylic acid (60 mg) was stirred for 2 hours at 100° to 120° C. After cooling, water (1 ml) was added to the reaction mixture and then concentrated. To the residue was added water (0.5 ml), adjusted to pH 7 with 1N aqueous sodium hydroxide solution and the solution was allowed to stand in a refrigerator. The resulting precipitate was collected by filtration and washed with water to give the title compound (33 mg) as colorless needles, mp 229°–232° C. (decompd.).

Analysis (%) for $C_{19}H_{22}FN_3O_4$; Calcd. (Found): C, 60.79 (60.80); H, 5.91 (5.90); N, 11.19 (11.15).

EXAMPLE 14

Synthesis of 1-cyclopropyl-6-fluoro-1,4-dihydro-8-methoxy-7-(3-methyl-1-piperazinyl)-4-oxo-3-quinolinecarboxylic acid To a solution of sodium methoxide prepared from sodium (0.4 g) and absolute methanol (20 ml) was added 1-cyclopropyl-6,8-difluoro-1,4-dihydro-7-(3-methyl-1-piperazinyl)-4-oxo-3-quinolinecarboxylic acid (1.12 g), and, the mixture in sealed tube was stirred for 70.5 hours at 140° to 150° C. and then concentrated. The residue was dissolved in small amount of water, the resulting solution was adjusted to pH 7 with acetic acid and concentrated. The resulting residue was purified by silica gel column chromatography eluting with chloroform-methanol-concentrated aqueous ammonia (20:6:1) and recrystallized from methanol to give the title compound (0.33 g) as pale yellow prisms, mp 162°- C.

Analysis (%) for $C_{19}H_{22}FN_3O_4 \cdot \frac{1}{2}\, H_2O$; Calcd. (Found): C, 59.37 (59.48); H, 6.03 (5.70); N, 10.93 (11.07).

H-NMR (δ in CDCl₃): 8.79 (1H, s, 2-position), 7.85 (1H, m, J=12.3 Hz, 5-position), 4.1–3.9 (1H, m,

3.77 (3H, s, OCH₃), 3.5–2.9 (7H, m, piperazine), 1.3–1.0 (7H, m,

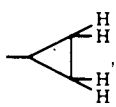

CH₃)

EXAMPLE 15

Synthesis of 7-(3-amino-1-pyrrolidinyl)-1-cyclopropyl-6-fluoro-1,4-dihydro-8-methoxy-4-oxo-3-quinolinecarboxylic acid To a solution of sodium methoxide prepare from sodium (0.2 g) and absolute methanol (10 ml) was added 7-(3-amino 1-pyrrolidinyl)-1-cyclopropyl-6,8-difluoro-1,4-dihydro-4-oxo-3quinolinecarboxylic acid (0.47 g) and the mixture in sealed tube was stirred for 49 hours at 140° to 150° C. and then concentrated. The residue was purified by silica gel column chromatography eluting with chloroform-methanol-concentrated aqueous ammonia (20:6:1) and recrystallized from a solution of dichloromethanemethanol (1:1) to give the title compound (6 mg as pale yellow prisms, mp 207.5°–212° C.

Analysis (%) for $C_{18}H_{20}FN_3O_4 \cdot H_2O$: Calcd. (Found): C, 56.99 (57.19); H, 5.82 (5.38); N, 11.13 (10.86).

Mass analysis (m/e): 361 (M⁺), 362 (M⁺+1).

H-NMR (δ in D₂O, NaOD): 8.48 (1H, s, 2-position), 7.62 (1H, d, J=14.5 Hz, 5-position), 4.1–3.9 (1H, m,

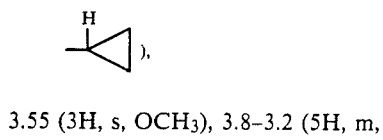

3.55 (3H, s, OCH₃), 3.8–3.2 (5H, m,

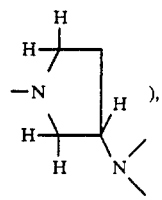

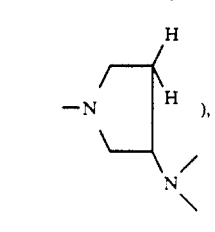

2.3–1.6 (2H, m,

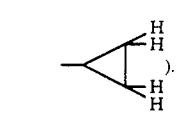

1.2–0.9 (4H, m,

EXAMPLE 16

Synthesis of 7-(3-amino-4-methyl-1-pyrrolidinyl)-1-cyclopropyl-6-fluoro-1,4-dihydro-8-methoxy-4-oxo-3-quinolinecarboxylic acid To a solution of sodium methoxide prepare from sodium (50 mg) and absolute methanol (3 ml) was added 7-(3-amino-4-methyl-1-pyrrolidinyl)-1-cyclopropyl-6,8-difluoro-1,4-dihydro-4-oxo-3-quinolinecarboxylic acid (80 mg) and the mixture in sealed tube was stirred for 86 hours at 140° to 150° C. and then concentrated. Small amount of water was added to the residue, and the solution was adjusted pH 7 with acetic acid and concentrated. The resulting residue was purified by silica gel column chromatography eluting with chloroform-methanol-concentrated aqueous ammonia (20:6:1) and recrystallized from a solution of dichloromethanemethanol (1:1) to give the title compound (9 mg) as pale yellow prisms, mp 191.5°–193.5° C.

Analysis (%) for C₁₉H₂₂FN₃O₄.7/5 H₂O; Calcd. (Found): C. 56.96 (57.10); H, 6.24 (5.98); N, 10.49 (10.42).

H-NMR (δ in D₂O, NaOD): 8.47 (1H, s, 2-position), 7.57 (1H, d, J=14.5 Hz, 5-position), 4.1–3.9 (1H, m,

3.51 (3H, s OCH₃), 3.8–3.2 (4H, m,

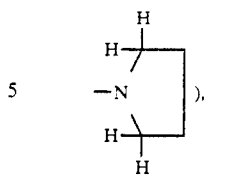

3.2–2.9 (1H, q,

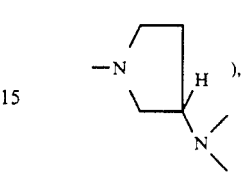

2.1–1.7 (1H, m,

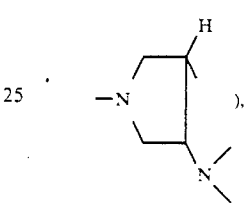

1.09 (3H, d, J=6.59 Hz,

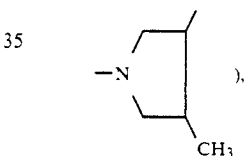

1.3–0.7 (4H, m,

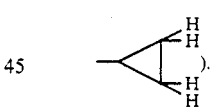

EXAMPLE 17

Synthesis of 7-(3-aminomethyl-1-pyrrolidinyl)-1-cyclopropyl-6-fluoro-1,4-dihydro-8-methoxy-4-oxo-3-quinolinecarboxylic acid To a solution of sodium methoxide prepare from sodium (0.2 g) and absolute methanol (9 ml) was added 7-(3-aminomethyl-1-pyrrolidinyl)-1-cyclopropyl-6,8-difluoro-1,4-dihydro-4-oxo-3-quinolinecarboxylic acid (0.5 g) and the mixture in sealed tube was stirred for 86 hours at 140° to 150° C. and then concentrated. Small amount of water was added to the residue, and the solution was adjusted pH 7 with acetic acid and then concentrated. The resulting residue was purified by silica gel column chromatography eluting with chloroform-methanol-concentrated aqueous ammonia (20:6:1) and recrystallized from methanol to give the title compound (40 mg) as pale yellow prisms, mp 225°–228.5° C. (decompd.).

Analysis (%) for $C_{19}H_{22}FN_3O_4 \cdot \frac{3}{4} H_2O$; Calcd. (Found): C, 58.91 (58.73); H, 6.07 (5.92); N, 10.85 (10.88).

EXAMPLE 18

Synthesis of 1-cyclopropyl-6-fluoro-1,4-dihydro-8-ethoxy-4-oxo-7-(1-piperazinyl)-3-quinolinecarboxylic acid To a solution of sodium ethoxide prepare from sodium (0.75 g) and absolute ethanol (30 ml) was added 1-cyclopropyl-6,8-difluoro-1,4-dihydro-4-oxo-7-(1-piperazinyl)-3-quinolinecarboxylic acid (0.8 g) and the mixture in sealed tube was stirred for 52 hours at 140° to 150° C. and then concentrated. Water (60 ml) was added to the residue, and the solution was adjusted pH 7 with acetic acid and extracted with chloroform. The chloroform layer was washed with saturated saline solution, dried over anhydrous sodium sulfate and then concentrated. The resulting residue was purified by silica gel column chromatography eluting with chloroform-methanol (2:1) → chloroform-methanol-concentrated aqueous ammonia (20:6:1 → 10:10:1) and recrystallized from ethanol to give the title compound (75 mg) as light brown prisms, mp 119°–122° C.

Analysis (%) for $C_{19}H_{22}FN_3O_4 \cdot \frac{1}{2} H_2O$; Calcd. (Found): C, 59.37 (59.60); H, 6.03 (6.04); N, 10.93 (10.85).

TEST EXAMPLE 1

Antibacterial spectra

The antibacterial test was carried out according to the method designated by Japan Society of Chemotherapy. The results are shown in Table 1.

TABLE 1-a

| | | In vitro antibacterial activity | | | |
| | | MIC (μg/ml) | | | |
| Organism ($10^6$ cells/ml) | Gram | Exp. 1 | Exp. 2 | Exp. 3 | Exp. 4 |
|---|---|---|---|---|---|
| Bacilus subtilis PCI 219 | + | 0.025 | 0.025 | 0.025 | 0.025 |
| Staphylococcus aureus 209 P | + | 0.10 | 0.10 | 0.10 | 0.05 |
| S. aureus IID 670 (Terajima) | + | 0.10 | 0.10 | 0.10 | 0.05 |
| S. aureus Smith | + | 0.10 | 0.10 | 0.10 | 0.05 |
| S. epidermidis IID 866 | + | 0.10 | 0.10 | 0.10 | 0.10 |
| Streptococcus pyogenes (S-8) | + | — | — | — | 0.05 |
| S. pyogenes IID 692 | + | — | — | — | 0.10 |
| S. pneumoniae IID 552 | + | — | — | — | 0.10 |
| E. faecalis IID 682 | + | — | — | — | 0.10 |
| Escherichia coli NIHJ JC-2 | — | ≦0.0063 | 0.0125 | ≦0.0063 | 0.0125 |
| E. coli ATCC 10536 | — | 0.025 | 0.025 | 0.0125 | 0.025 |
| E. coli ML 4707 | — | 0.025 | 0.025 | 0.0125 | 0.025 |
| Proteus vulgaris IFO 3167 | — | 0.0125 | 0.025 | 0.025 | 0.025 |
| P. mirabilis IID 994 | — | 0.025 | 0.05 | 0.025 | 0.05 |
| Morganella morganii IID 602 | — | 0.05 | 0.10 | 0.10 | 0.05 |
| Klebsiella pneumoniae KY(GN)6445 | — | 0.025 | 0.05 | 0.025 | 0.05 |
| K. pneumoniae 1-220S | — | 0.05 | 0.10 | 0.05 | 0.05 |
| Enterobacter cloacae IID 977 | — | 0.05 | 0.10 | 0.05 | 0.05 |
| Citrobacter freundii IID 976 | — | 0.025 | 0.05 | 0.025 | 0.05 |
| Serratia marcescens IID 618 | — | 0.05 | 0.10 | 0.10 | 0.05 |
| Shigella sonnei IID 969 | — | 0.0125 | 0.025 | 0.0125 | 0.025 |
| Salmonella enteritidis IID 604 | — | 0.05 | 0.10 | 0.05 | 0.05 |
| Pseudomonas aeruginosa V-1 | — | 0.10 | 0.39 | 0.20 | 0.39 |
| P. aeruginosa IFO 12689 | — | 0.78 | 1.56 | 1.56 | 0.39 |
| P. aeruginosa IID 1210 | — | 0.39 | 1.56 | 1.56 | 0.39 |
| P. cepacia GIFU 518 | — | 0.78 | 1.56 | 1.56 | 0.39 |
| P. maltophilia GIFU 2491 | — | 0.39 | 0.20 | 0.20 | 0.10 |
| Yersinia enterocolitica IID 981 | — | 0.05 | 0.10 | 0.05 | 0.05 |
| Acinetobacter anitratus IID 876 | — | 0.10 | 0.10 | 0.10 | 0.05 |
| Alcaligenes faecalis 0114002 | — | 0.20 | 0.39 | 0.39 | 0.39 |

TABLE 1-b

| | | In vitro antibacterial activity | | | |
| | | MIC (μg/ml) | | | |
| Organism ($10^6$ cells/ml) | Gram | Exp. 1 | Exp. 2 | Exp. 3 | Exp. 4 |
|---|---|---|---|---|---|
| Bacteroides fragilis GM 7000 | — | 0.78 | 0.39 | 0.39 | 0.20 |
| B. fragilis 0558 | — | 0.39 | 0.20 | 0.39 | 0.10 |
| B. fragilis 25285 | — | 0.39 | 0.39 | 0.39 | 0.10 |
| B. distasonis 8503 | — | 1.56 | 0.39 | 0.78 | 0.78 |
| B. thetaiotaomicron (0661) | — | 1.56 | 1.56 | 0.78 | 0.20 |
| B. vulgatus KYA 29327 | ± | 0.78 | 0.39 | 0.78 | 0.39 |
| Fusobacterium mortiferum 4249 | — | 0.39 | 0.78 | 0.78 | 0.20 |
| F. necrophorum S-45 | — | 0.39 | 0.78 | 0.39 | 0.20 |
| F. varium KYA 8501 | — | 3.13 | 6.25 | 6.25 | 1.56 |
| Eubacterium lentum GAI 5242 | + | 0.20 | 0.20 | 0.20 | 0.10 |
| Propionibacterium acens 11828 | + | 3.13 | 6.25 | 6.25 | 1.56 |
| Peptococcus magnus KY 017 | + | 0.20 | 0.20 | 0.20 | 0.10 |
| Clostridium difficile I-E | + | 3.13 | 1.56 | 3.13 | 0.39 |
| C. perfringens KYA 13123 | + | 0.39 | 0.39 | 0.39 | 0.20 |
| C. ramosum | + | 3.13 | 3.13 | 3.13 | 0.78 |
| Peptostreptococcus anaerobius KYA 27337 | + | 0.39 | 0.78 | 0.39 | 0.20 |
| Pst. micros UPI 5464-1 | + | 0.20 | 0.39 | 0.20 | 0.20 |

TABLE 1-b-continued

| | | In vitro antibacterial activity | | | |
|---|---|---|---|---|---|
| | | MIC (μg/ml) | | | |
| Organism (10⁶ cells/ml) | Gram | Exp. 1 | Exp. 2 | Exp. 3 | Exp. 4 |
| Veillonella parvula KYA 10790 | − | 0.20 | 0.39 | 0.20 | 0.20 |

TABLE 1-c

| | | In vitro antibacterial activity | | | |
|---|---|---|---|---|---|
| | | MIC (μg/ml) | | | |
| Organism (10⁶ cells/ml) | Gram | Exp. 5 | Exp. 6 | Exp. 7 | Exp. 8 |
| Bacilus subtilis PCI 219 | + | 0.0125 | 0.0125 | 0.025 | 0.025 |
| Staphylococcus aureus 209 P | + | 0.025 | 0.025 | 0.025 | 0.05 |
| S. aureus IID 670 (Terajima) | + | 0.05 | 0.05 | 0.025 | 0.05 |
| S. aureus Smith | + | 0.05 | 0.05 | 0.05 | 0.05 |
| S. epidermidis IID 866 | + | 0.10 | 0.10 | 0.05 | 0.05 |
| Streptococcus pyogenes (S-8) | + | 0.10 | 0.05 | — | 0.05 |
| S. pyogenes IID 692 | + | 0.10 | 0.10 | — | 0.05 |
| S. pneumoniae IID 552 | + | 0.10 | 0.10 | — | 0.05 |
| E. faecalis IID 682 | + | 0.10 | 0.10 | — | 0.05 |
| Escherichia coli NIHJ JC-2 | − | 0.0125 | 0.0125 | 0.025 | 0.025 |
| E. coli ATCC 10536 | − | 0.0125 | 0.0125 | 0.05 | 0.05 |
| E. coli ML 4707 | − | 0.025 | 0.0125 | 0.05 | 0.05 |
| Proteus vulgaris IFO 3167 | − | 0.025 | 0.05 | 0.05 | 0.05 |
| P. mirabilis IID 994 | − | 0.05 | 0.05 | 0.05 | 0.05 |
| Morganella morganii IID 602 | − | 0.05 | 0.10 | 0.20 | 0.39 |
| Klebsiella pneumoniae KY(GN)6445 | − | 0.025 | 0.05 | 0.05 | 0.05 |
| K. pneumoniae 1-220S | − | 0.05 | 0.05 | 0.10 | 0.10 |
| Enterobacter cloacae IID 977 | − | 0.05 | 0.05 | 0.10 | 0.20 |
| Citrobacter freundii IID 976 | − | 0.05 | 0.05 | 0.05 | 0.05 |
| Serratia marcescens IID 618 | − | 0.05 | 0.05 | 0.20 | 0.20 |
| Shigella sonnei IID 969 | − | 0.025 | 0.0125 | 0.05 | 0.05 |
| Salmonella enteritidis IID 604 | − | 0.05 | 0.05 | 0.05 | 0.10 |
| Pseudomonas aeruginosa V-1 | − | 0.78 | 0.78 | 0.20 | 0.78 |
| P. aeruginosa IFO 12689 | − | 0.78 | 0.78 | 0.78 | 3.13 |
| P. aeruginosa IID 1210 | − | 0.78 | 0.78 | 0.78 | 12.5 |
| P. cepacia GIFU 518 | − | 0.78 | 0.39 | 0.78 | 1.56 |
| P. maltophilia GIFU 2491 | − | 0.10 | 0.05 | 0.20 | 0.39 |
| Yersinia enterocolitica IID 981 | − | 0.05 | 0.05 | 0.10 | 0.10 |
| Acinetobacter anitratus IID 876 | − | 0.05 | 0.05 | 0.05 | 0.20 |
| Alcaligenes faecalis 0114002 | − | 0.20 | 0.20 | 0.39 | 1.56 |

TABLE 1-d

| | | In vitro antibacterial activity | | | |
|---|---|---|---|---|---|
| | | MIC (μg/ml) | | | |
| Organism (10⁶ cells/ml) | Gram | Exp. 5 | Exp. 6 | Exp. 7 | Exp. 8 |
| Bacteroides fragilis GM 7000 | − | 0.10 | 0.10 | 0.39 | 0.39 |
| B. fragilis 0558 | − | 0.10 | 0.10 | 0.20 | 0.39 |
| B. fragilis 25285 | − | 0.10 | 0.10 | 0.20 | 0.39 |
| B. distasonis 8503 | − | 0.39 | 0.39 | 0.78 | 3.13 |
| B. thetaiotaomicron (0661) | − | 0.10 | 0.20 | 0.39 | 3.13 |
| B. vulgatus KYA 29327 | − | 0.20 | 0.20 | 0.39 | 3.13 |
| Fusobacterium mortiferum 4249 | − | 0.20 | 0.20 | 0.20 | 0.39 |
| F. necrophorum S-45 | − | 0.20 | 0.20 | 0.20 | 0.39 |
| F. varium KYA 8501 | − | 1.56 | 1.56 | 0.78 | 3.13 |
| Eubacterium lentum GAI 5242 | + | ≦0.05 | ≦0.05 | 0.39 | 0.20 |
| Propionibacterium acens 11828 | + | 1.56 | 3.13 | 0.39 | 0.78 |
| Peptococcus magnus KY 017 | + | 0.10 | ≦0.05 | 0.05 | ≦0.05 |
| Clostridium difficile I-E | + | 0.39 | 0.78 | 0.39 | — |
| C. perfringens KYA 13123 | + | 0.20 | 0.20 | 0.20 | 0.20 |
| C. ramosum | + | 0.78 | 0.78 | 0.78 | 0.39 |
| Peptostreptococcus anaerobius KYA 27337 | + | 0.20 | 0.10 | 0.05 | 0.20 |
| Pst. micros UPI 5464-1 | + | 0.20 | 0.20 | 0.10 | 0.39 |
| Veillonella parvula KYA 10790 | − | 0.20 | 0.20 | 0.10 | 0.39 |

TABLE 1-e

| | | In vitro antibacterial activity | | | |
|---|---|---|---|---|---|
| | | MIC (μg/ml) | | | |
| Organism (10⁶ cells/ml) | Gram | Exp. 9 | Exp. 10 | Exp. 11 | Exp. 18 |
| Bacilus subtilis PCI 219 | + | 0.0063 | 0.025 | 0.0125 | ≦0.05 |
| Staphylococcus aureus 209 P | + | 0.0125 | 0.05 | 0.025 | 0.20 |
| S. aureus IID 670 (Terajima) | + | 0.0125 | 0.10 | 0.05 | 0.39 |
| S. aureus Smith | + | 0.0125 | 0.10 | 0.025 | 0.39 |

TABLE 1-e-continued

In vitro antibacterial activity

| Organism (10⁶ cells/ml) | Gram | MIC ($\mu$g/ml) | | | |
|---|---|---|---|---|---|
| | | Exp. 9 | Exp. 10 | Exp. 11 | Exp. 18 |
| S. epidermidis IID 866 | + | 0.025 | — | — | 0.39 |
| Streptococcus pyogenes (S-8) | + | 0.025 | 0.39 | 0.20 | 1.56 |
| S. pyogenes IID 692 | + | 0.05 | >0.78 | 0.39 | 3.13 |
| S. pneumoniae IID 552 | + | 0.025 | >0.78 | 0.20 | 0.78 |
| E. faecalis IID 682 | + | 0.05 | 0.39 | 0.20 | 1.56 |
| Escherichia coli NIHJ JC-2 | — | 0.0063 | 0.025 | 0.025 | ≦0.05 |
| E. coli ATCC 10536 | — | 0.025 | 0.05 | 0.025 | ≦0.05 |
| E. coli ML 4707 | — | 0.025 | 0.05 | 0.025 | ≦0.05 |
| Proteus vulgaris IFO 3167 | — | 0.025 | 0.10 | 0.20 | ≦0.05 |
| P. mirabilis IID 994 | — | 0.025 | 0.20 | 0.10 | 0.10 |
| Morganella morganii IID 602 | — | 0.20 | 0.20 | 0.20 | 0.39 |
| Klebsiella pneumoniae KY(GN)6445 | — | 0.05 | 0.05 | 0.05 | ≦0.05 |
| K. pneumoniae 1-220S | — | 0.10 | 0.20 | 0.20 | 0.20 |
| Enterobacter cloacae IID 977 | — | 0.10 | 0.20 | 0.05 | 0.20 |
| Citrobacter freundii IID 976 | — | 0.055 | 0.05 | 0.05 | 0.10 |
| Serratia marcescens IID 618 | — | 0.10 | 0.20 | 0.20 | 0.20 |
| Shigella sonnei IID 969 | — | 0.025 | 0.025 | 0.025 | ≦0.05 |
| Salmonella enteritidis IID 604 | — | 0.05 | 0.20 | 0.10 | 0.10 |
| Pseudomonas aeruginosa V-1 | — | 0.39 | 0.39 | 0.78 | 0.78 |
| P. aeruginosa IFO 12689 | — | 1.56 | 1.56 | 1.56 | 3.13 |
| P. aeruginosa IID 1210 | — | 6.25 | 1.56 | 1.56 | 6.25 |
| P. cepacia GIFU 518 | — | 0.78 | 1.56 | 1.56 | 3.13 |
| P. maltophilia GIFU 2491 | — | 0.20 | 0.20 | 0.20 | 0.39 |
| Yersinia enterocolitica IID 981 | — | 0.10 | 0.20 | 0.10 | 0.20 |
| Acinetobacter anitratus IID 876 | — | 0.05 | 0.10 | 0.05 | 0.10 |
| Alcaligenes faecalis 0114002 | — | 0.78 | 0.78 | 0.78 | 0.78 |

TABLE 1-f

In vitro antibacterial activity

| Organism (10⁶ cells/ml) | Gram | MIC ($\mu$g/ml) | | | |
|---|---|---|---|---|---|
| | | Exp. 9 | Exp. 10 | Exp. 11 | Exp. 18 |
| Bacteroides fragilis GM 7000 | — | 0.10 | 3.13 | 1.56 | 3.13 |
| B. fragilis 0558 | — | 0.10 | 3.13 | 1.56 | 12.5 |
| B. fragilis 25285 | — | 0.10 | 3.13 | 1.56 | 3.13 |
| B. distasonis 8503 | — | 0.78 | 6.25 | 12.5 | 12.5 |
| B. thetaiotaomicron (0661) | — | 0.78 | 6.25 | 1.56 | 12.5 |
| B. vulgatus KYA 29327 | — | 0.39 | 0.39 | 0.78 | 12.5 |
| Fusobacterium mortiferum 4249 | — | 0.20 | 1.56 | 3.13 | 3.13 |
| F. necrophorum S-45 | — | 0.20 | 1.56 | 1.56 | 3.13 |
| F. varium KYA 8501 | — | 1.56 | 50 | 25 | 25 |
| Eubacterium lentum GAI 5242 | + | 0.10 | 0.78 | 0.39 | 1.56 |
| Propionibacterium acens 11828 | + | 1.56 | 12.5 | 6.25 | 12.5 |
| Peptococcus magnus KY 017 | + | ≦0.05 | 1.56 | 0.78 | 0.78 |
| Clostridium difficile I-E | + | — | — | — | — |
| C. perfringens KYA 13123 | + | ≦0.05 | 3.13 | 0.78 | 1.56 |
| C. ramosum | + | 0.20 | 1.56 | 1.56 | — |
| Peptostreptococcus anaerobius KYA 27337 | + | ≦0.05 | 1.56 | 0.78 | 3.13 |
| Pst. micros UPI 5464-1 | + | 0.39 | 0.39 | 0.78 | 0.78 |
| Veillonella parvula KYA 10790 | — | 0.39 | 0.39 | 0.78 | 0.78 |

TABLE 1-g

In vitro antibacterial activity

| Organism (10⁶ cells/ml) | Gram | MIC (g/ml) | |
|---|---|---|---|
| | | CPFX | MNZ |
| Bacillus subtilis PCI 219 | + | 0.05 | — |
| Staphylococcus aureus 209 P | + | 0.20 | — |
| S. aureus IID 670 (Terajima) | + | 0.20 | — |
| S. aureus Smith | + | 0.39 | — |
| S. epidermidis IID 866 | + | 0.20 | — |
| Streptococcus pyogenes (S-8) | + | 0.39 | — |
| S. pyogenes IID 692 | + | 0.78 | — |
| S. pneumoniae IID 552 | + | 0.78 | — |
| E. faecalis IID 682 | + | 0.78 | — |
| Escherichia coli NIHJ JC-2 | — | 0.0063 | — |
| E. coli ATCC 10536 | — | 0.0125 | — |
| E. coli ML 4707 | — | 0.0125 | — |
| Proteus vulgaris IFO 3167 | — | 0.0125 | — |
| P. mirabilis IID 994 | — | 0.0125 | — |
| Morganella morganii IID 602 | — | 0.025 | — |
| Klebsiella pneumoniae KY(GN)6445 | — | 0.0125 | — |
| K. pneumoniae 1-220S | — | 0.025 | — |
| Enterobacter cloacae IID 977 | — | 0.025 | — |
| Citrobacter freundii IID 976 | — | 0.0063 | — |
| Serratia marcescens IID 618 | — | 0.025 | — |
| Shigella sonnei IID 969 | — | 0.0063 | — |
| Salmonella enteritidis IID 604 | — | 0.025 | — |
| Pseudomonas aeruginosa V-1 | — | 0.05 | — |
| P. aeruginosa IFO 12689 | — | 0.20 | — |
| P. aeruginosa IID 1210 | — | 0.78 | — |
| P. cepacia GIFU 518 | — | 0.39 | — |
| P. maltophilia GIFU 2491 | — | 0.39 | — |
| Yersinia enterocolitica IID 981 | — | 0.025 | — |
| Acinetobacter anitratus IID 876 | — | 0.10 | — |
| Alcaligenes faecalis 0114002 | — | 0.39 | — |

TABLE 1-h

| | | In vitro antibacterial activity | |
|---|---|---|---|
| | | MIC (g/ml) | |
| Organism ($10^6$ cells/ml) | Gram | CPFX | MNZ |
| *Bacteroides fragilis* GM 7000 | − | 6.25 | 0.78 |
| *B. fragilis* 0558 | − | 3.13 | 0.78 |
| *B. fragilis* 25285 | − | 3.13 | 0.78 |
| *B. distasonis* 8503 | − | 6.25 | 0.39 |
| *B. thetaiotaomicron* (0661) | − | >12.5 | 0.78 |
| *B. vulgatus* KYA 29327 | − | >12.5 | 0.39 |
| *Fusobacterium mortiferum* 4249 | − | 1.56 | 0.20 |
| *F. necrophorum* S-45 | − | 0.78 | — |
| *F. varium* KYA 8501 | − | >12.5 | 0.39 |
| *Eubacterium lentum* GAI 5242 | + | 0.78 | 0.10 |
| *Propionibacterium acens* 11828 | + | 12.5 | 0.78 |
| *Peptococcus magnus* KY 017 | + | 0.39 | 0.78 |
| *Clostridium difficile* I-E | + | 12.5 | 0.20 |
| *C. perfringens* KYA 13123 | + | 0.39 | 0.10 |
| *C. ramosum* | + | 12.5 | 0.39 |
| *Peptostreptococcus anaerobius* KYA 27337 | + | 1.56 | — |
| *Pst. micros* UPI 5464-1 | + | 0.20 | 0.78 |
| *Veillonella parvula* KYA 10790 | − | 0.20 | 0.78 |

Contrast compounds
CPFX: Ciprofloxacin
MNZ: Metronidazole

The compounds of the invention was more excellent against gram-positive bacteria than ciprofloxacin known hitherto and exhibited high activity anaerobic bacteria equal to metronidazole being recommended by medical specialists.

What is claimed is:
1. A compound of the formula:

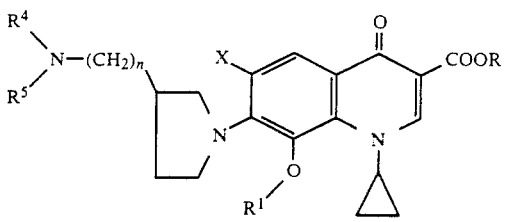

wherein $R^1$ is lower alkyl, X is halogen, R is hydrogen or lower alkyl, n is 0 or 1, $R^4$ is hydrogen, lower alkyl or substituted lower alkyl and $R^5$ is hydrogen, lower alkyl, acyl, or alkoxy carbonyl.

2. The compound of claim 1 which is 7-(3-amino-1-pyrrolidinyl)-1-cyclopropyl-6-fluoro-1,4-dihydro-8-methoxy-4-oxo-3-quinolinecarboxylic acid.

3. The compound of claim 1 which is 7-(3-aminomethyl-1-pyrrolidinyl)-1-cyclopropyl-6-fluoro-1,4-dihydro-8-methoxy-4-oxo-3-quinolinecarboxylic acid.

4. The compound of claim 1 which is 1-cyclopropyl-6-fluoro-1,4-dihydro-8-methoxy-7-(3-methylaminomethyl-1-pyrrolidinyl)-4-oxo-3-quinolinecarboxylic acid.

5. The compound of claim 1 which is 1-cyclopropyl-7-(3-ethylaminomethyl-1-pyrrolidinyl)-b 6-fluoro-1,4-dihydro-8-methoxy-4-oxo-3-quinolinecaboxylic acid.

* * * * *